(12) United States Patent
Dahl et al.

(10) Patent No.: US 6,496,712 B1
(45) Date of Patent: Dec. 17, 2002

(54) METHOD AND APPARATUS FOR ELECTROPHYSIOLOGY CATHETER WITH ENHANCED SENSING

(75) Inventors: Roger Dahl, Andover, MN (US); Steven Savage, Paynesville, MN (US)

(73) Assignee: Biosense Webster, Inc., Diamond Bar, CA (US)

( * ) Notice: Subject to any disclaimer, the term of this patent is extended or adjusted under 35 U.S.C. 154(b) by 0 days.

(21) Appl. No.: 09/562,293

(22) Filed: May 1, 2000

(51) Int. Cl.$^7$ ............................................... A61B 5/042
(52) U.S. Cl. ......................... 600/374; 600/395; 600/509
(58) Field of Search ................... 600/374, 375, 600/395, 397, 509; 607/122, 127, 126

(56) References Cited

U.S. PATENT DOCUMENTS

| | | | | |
|---|---|---|---|---|
| 4,011,861 A | | 3/1977 | Enger | 128/2.06 E |
| 4,603,704 A | * | 8/1986 | Mund et al. | 607/122 |
| 4,979,510 A | * | 12/1990 | Franz et al. | 600/374 |
| 5,575,814 A | * | 11/1996 | Giele et al. | 607/127 |
| 5,579,764 A | | 12/1996 | Goldreyer | 128/642 |
| 5,587,200 A | * | 12/1996 | Lorenz et al. | 427/2.24 |
| 5,824,030 A | * | 10/1998 | Yang et al. | 607/122 |
| 6,152,882 A | * | 11/2000 | Prutchi | 600/509 |
| 6,263,250 B1 | * | 7/2001 | Skinner | 607/126 |

FOREIGN PATENT DOCUMENTS

| | | | |
|---|---|---|---|
| EP | 0 453 117 A | 10/1991 | A61N/1/05 |
| EP | 0 664 990 A | 8/1995 | A61B/5/042 |

OTHER PUBLICATIONS

Biotronik Web Page Printout, printed Sep. 28, 1999; "http://www.biotronik.com/products/electro/ablation/ablation.html".

In Vivo Performance of a New Micro/Macro–Porous, Titanium Nitride Coated Electrode by Shawn Moaddeb, M.S., John Helland, B.M.E., Ron Forino, Siemens Pacesetter®, Inc., Sylmar, CA, U.S.A.

* cited by examiner

*Primary Examiner*—Lee Cohen
(74) *Attorney, Agent, or Firm*—Nawrocki, Rooney & Sivertson, P.A.

(57) ABSTRACT

A method of and an apparatus for performing electrophysiological mapping of myocardial tissue. An electrode at a distal portion of a sensing catheter electrically contacts the tissue permitting the catheter to conduct a sensed signal to analysis and display equipment. The electrode is formed of a biocompatible metal. This basic structure is coated with a material with micro texturizes the electrode surface to increase the effective surface area without significantly increasing the electrode footprint.

19 Claims, 3 Drawing Sheets

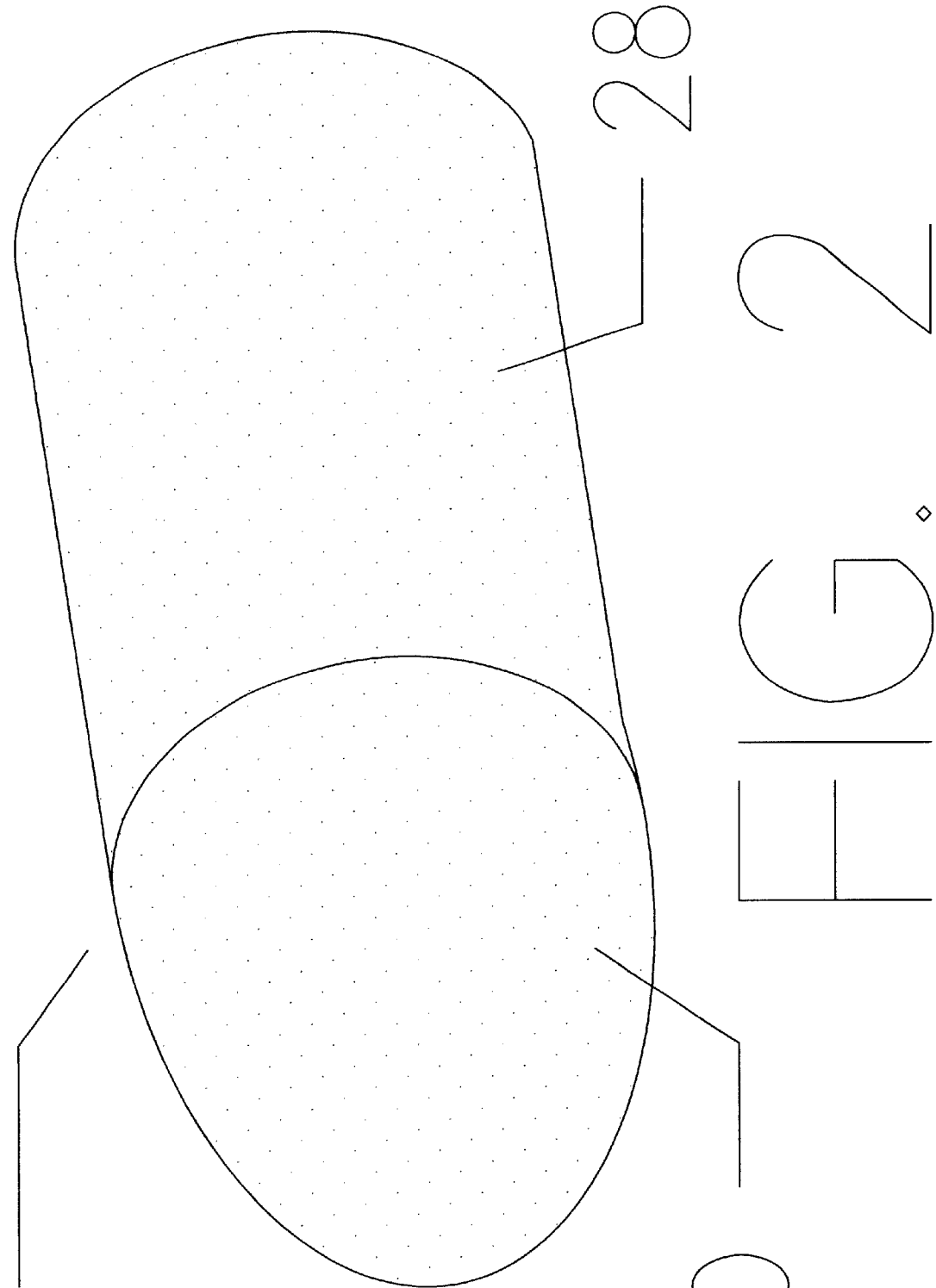

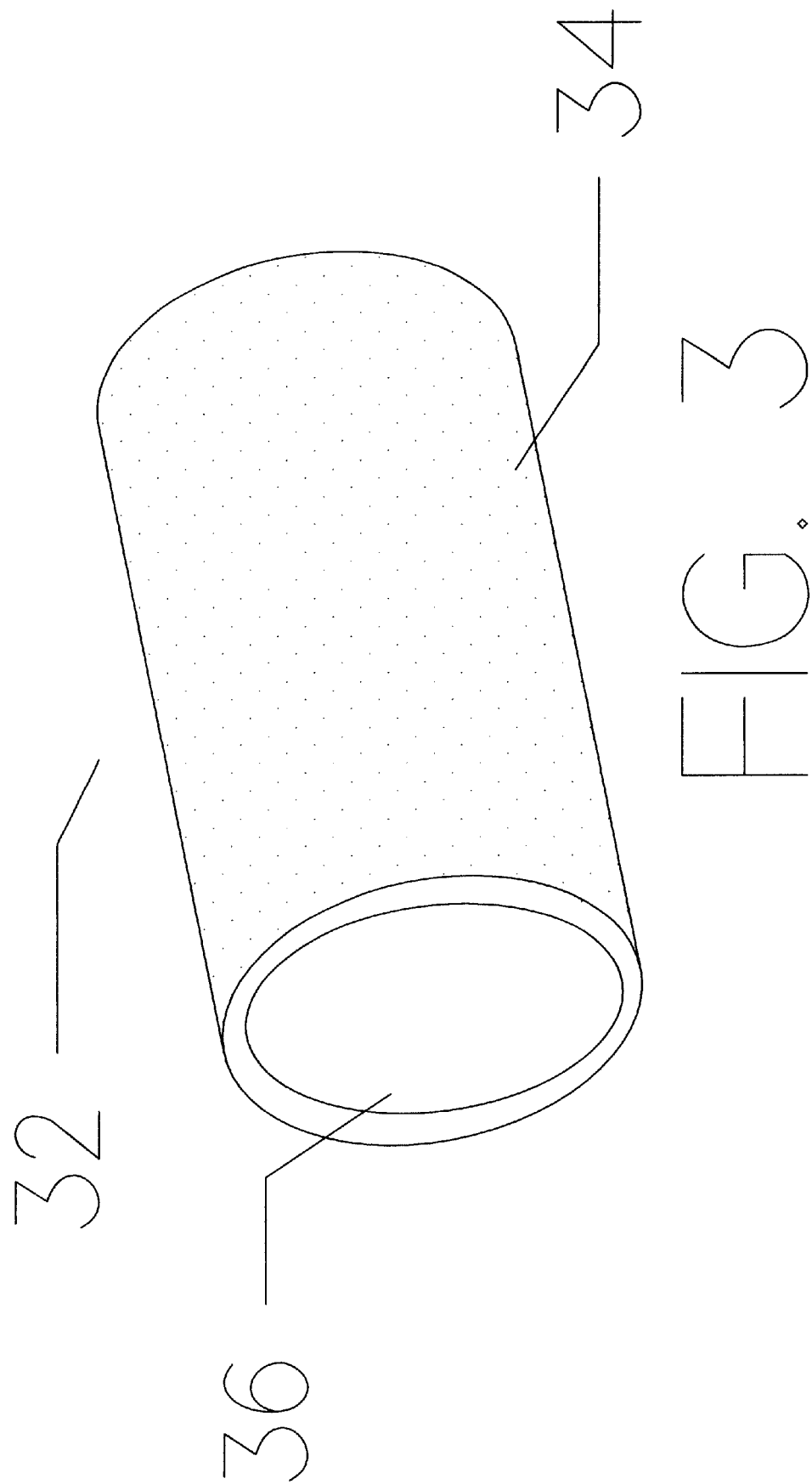

METHOD AND APPARATUS FOR ELECTROPHYSIOLOGY CATHETER WITH ENHANCED SENSING

CROSS REFERENCE TO CO-PENDING APPLICATIONS

None.

BACKGROUND OF THE INVENTION

1. Field of the Invention

The present invention generally relates to medical devices, and more particularly relates to devices for diagnosing various cardiac conditions.

2. Description of the Prior Art

It is well known in the prior art to design and build apparatus for the diagnosis of various cardiac disorders. Certain symptomatic chronic conditions are quite easily identified and diagnosed. However, various intermittent conduction disorders may require substantial diagnostic testing and analysis.

Some of the most difficult diagnoses are associated with intermittent conduction conditions. Typically, such disorders may cause tachycardia (i.e.,too fast heart beat), as well as bradycardia (i.e., too slow heart beat), and potentially even cardiac arrest (i.e., no heart beat) and fibrillation (i.e., uncontrolled super fast heat activity). These conditions range from extremely serious to fatal. Therefore, it is important to diagnose and treat the underlying pathology before any of these symptoms appear in environments not having emergency treatment resources.

One current approach, which is particularly useful in the diagnosis of these intermittent cardiac conduction disorders, is electrophysiological (EP) mapping. In accordance with this technique, the patient is taken to a catheter laboratory in which catheters are passed into the interior of the heart. These electrically conductive catheters permit instruments to analyze and record the electrical activity at points within the myocardium which are in contact with one or more electrodes of the catheter. In a typical diagnostic catheter, a single electrode is positioned at the distal end of the catheter. Each repositioning of the distal end of the catheter permits measurement of electrical activity at another myocardial location. In another version, multiple electrodes are located in a basket-like arrangement that expands inside the heart to bring the electrodes into contact with the myocardium. The electrical activity of the myocardium is "mapped" by the recording of electrical activity as a function of electrode position in contact with the myocardium.

Electrophysiological mapping permits the diagnostician to view each physical location within the myocardium exhibiting improper and suspect electrical activity. Following diagnosis, typical treatments include: management with medication; ablation of improperly functioning myocardial tissue; implantation of a medical device to treat conduction deficiencies (e.g., pacemaker, cardioverter, etc.); more invasive surgical procedure; or a combination of these procedures.

Typically, sensing electrodes are made from metal rings or cylindrical plugs made from biocompatible grade metal alloys like platinum and stainless steel. Some designs use a sintered metal made from micron sized metal particles which are hydraulically pressed together and then fired to obtain the requisite strength.

A particular problem with electrophysiological mapping catheters arises because of the low level of the electrical signals derived from the contact between the myocardium and a relative small geometry electrode. One solution to low electrical signals from a sensing electrode that is used for long-term, chronic sensing and stimulation is to increase the size of the electrode in contact with the myocardium. However, increasing the size of the electrode for an electrophysiological mapping catheter creates a greater sensing footprint on the myocardial surface, which decreases the resolution of the mapping process.

SUMMARY OF THE INVENTION

The present invention overcomes many of the disadvantages found in the prior art by providing a method of and apparatus for an electrophysiological catheter that increases the signal strength derived during the mapping process without increasing the electrode footprint in contact with the myocardial tissue. The technique is useful with both ring type and cylindrical plug type electrode constructions. It may be utilized with virtually any suitable electrode material or electrode configuration.

In accordance with the preferred mode of the present invention, a coating is applied to the exterior surface of the electrode structure to greatly increase the effective surface contact area without appreciably changing the contact footprint. However, unlike electrodes for chronic sensing and stimulation, this coating is selected to optimize acute sensing, rather than enhance chronic positional stability via tissue ingrowth or improved stimulation current densities.

Preferably, the coating is of a different material from the electrode structure. Titanium nitride (TiN) is the preferred material. The coating is applied at a thickness of from several angstroms to several millimeters. The coated surface may be continuous or discrete.

This coated surface layer creates a micro texturing which substantially increases the effective surface area in direct proximity to the tissue. The enhanced surface contact produces a sharper sensed signal due to decreased polarization thereby reducing the amount of capacitive coupling and increasing the signal-to-noise ratio. However, this larger effective surface contact area retains essentially the same footprint as the uncoated electrode. Therefore, the resolution of the mapping process is not adversely effected.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein:

FIG. 2 is a closeup view of a ring type electrode according to the present invention; and FIG. 3 is a closeup view of a cylindrical plug type electrode according to the present invention.

DETAILED DESCRIPTION OF THE PREFERRED EMBODIMENTS

Figure 1:
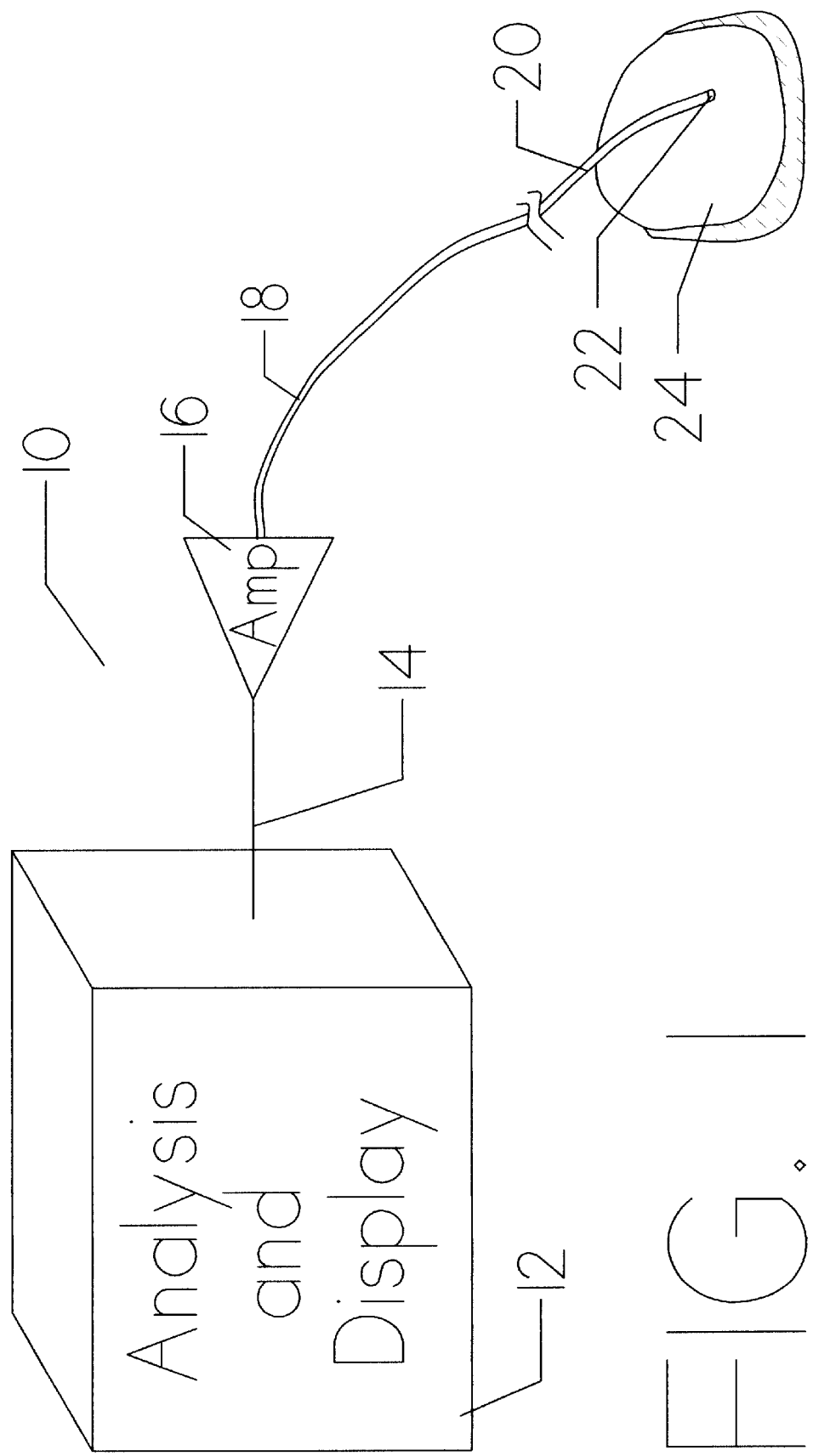
FIG. 1 is a diagram showing the major components of the overall electrophysiological mapping system.

FIG. 1 is a diagram showing the major components of a preferred embodiment of the overall electrophysiological mapping system 10. Distal portion 20 of catheter 18, employing the preferred mode of the present invention, is inserted into the appropriate blood vessel and advanced under fluoroscopy until electrode 22 is in physical and electrical contact with or in close proximity to myocardial tissue 24 (shown as a section). Electrical activity sensed by electrode 22 generates a corresponding signal which is transferred via electrically conductive catheter 18 to amplifier 16.

In this embodiment, electrode 22 is repositioned in relation to myocardial tissue 24 to produce corresponding signals from other portions of the myocardium. In an alternate embodiment (not shown), a plurality of electrode 22 may be arranged in a basket or helical configuration as is known in the art, to produce multiple corresponding signals simultaneously without necessarily requiring that the electrodes be repositioned in relation to myocardial tissue 24. Under typical conditions, the corresponding signal is of sufficiently low amplitude that substantial amplification by amplifier 16 is required.

The amplified signal is conducted from amplifier 16 to analysis and display equipment 12 via cable 14. Analysis and display equipment 12 processes and records the amplified signal, which when presented as a function of time (i.e., electrode position in relation to myocardial tissue 24), results in the electrophysiologic map of myocardial tissue 24. Analysis and display equipment 12 is readily available on the commercial market as is well known to those of skill in the art. It is important, however, that such equipment have a low impedance input so as not to degenerate or distort the high quality signal provided by the electrodes of the present invention. Once the procedure is complete, catheter 18 is withdrawn and electrode 22 is no longer in physical or electrical contact with myocardial tissue 24.

In one embodiment, the acute procedure for creating the electrophysiologic map of myocardial tissue 24 using mapping system 10 is performed separate from any therapy or treatment for a condition diagnosed as a result generating the electrophysiologic map. In another embodiment, catheter 18 may be provided with an ablation electrode or other device for delivering therapy or treatment as a part of a single acute procedure. In this case, it is contemplated that mapping system 10 may be used during and after delivery of myocardial tissue 24 or to verify the effectiveness of the therapy or treatment.

FIG. 2 is close up view of ring type electrode 26, which is a first embodiment of electrode 22 (see also FIG. 1). It contains a first cylindrical portion 28 and a conical distal portion 30. Both the cylindrical portion 28 and the conical distal portion 30 are preferably made of a titanium or other suitable biocompatible metal. Both portions are coated with Titanium Nitride (TiN) to produce the micro texturing as shown. Preferably, the coating is about 500 microns in thickness. The coating is applied by sintering to preserve the electrical conductivity of the structure. A conductor or wire (not shown) is electrically coupled to the interior of ring type electrode 26 to conduct the sensed signal to amplifier 16 (see also FIG. 1).

FIG. 3 is a close up view of electrode assembly 32, which is a cylindrical version of electrode 22 ( see also FIG. 1). Electrode assembly 32 is preferably a titanium cylinder having an inner lumen 36 of sufficient dimension to conveniently mount at the distal portion 20 of catheter 18. A coating of Titanium Nitride (TiN) is sintered to the exterior surface of the titanium cylinder producing the micro texturized surface as shown. The coating may be attached by other means but must preserve the electrical conductivity of electrode assembly 32. A conductor (not shown) is electrically coupled to the interior of lumen 36 for conduction of the signal along the length of catheter 18.

Alternatively, the coating may be comprised of micro-textured platinum on platinum (i.e., platinum black or rainy platinum). In another embodiment, the coating is applied to a porous or grossly roughened surface of approximately the same footprint to further enhance the effect produced by the present invention.

Having thus described the preferred embodiments of the present invention, those of skill in the art will readily appreciate that the teachings found herein may be applied to yet other embodiments within the scope of the claims hereto attached.

What is claimed is:

1. In an electrophysiological mapping system including analysis and display equipment responsively coupled to a catheter having a distal portion, the improvement comprising:

an electrode having an outer surface physically mounted on said distal portion of said catheter and responsively coupled to said analysis and display equipment wherein said outer surface of said electrode is micro texturized which increases the effective surface area while reducing the amount of capacitive coupling.

2. The improvement according claim 1 wherein said electrode further comprises a substrate and an outer coating.

3. The improvement according to claim 2 wherein said outer coating has a thickness of several angstroms to several millimeters.

4. The improvement according to claim 3 wherein said outer coating further comprises Titanium Nitride.

5. The improvement according to claim 4 wherein said substrate further comprises a conductive metal.

6. An apparatus comprising:
   a. Analysis and display equipment;
   b. A catheter responsively coupled to said analysis and display equipment wherein said catheter has a distal portion; and
   c. An electrode responsively coupled to said distal portion of said catheter and said analysis and display equipment wherein said electrode further comprises a micro texture outer surface which increases the effective surface area while reducing the amount of capacitive coupling.

7. An apparatus according to claim 6 wherein said electrode further comprises a substrate and a coating.

8. An apparatus according to claim 7 wherein said substrate is selected from the group consisting of smooth surface, porous surface and textured surface.

9. An apparatus according to claim 6 wherein said electrode is selected from the group consisting of a cylindrical plug type electrode, a spherical electrode, a semi-spherical electrode, a ring electrode, and a partial ring electrode.

10. An apparatus according to claim 7 wherein said coating is selected from the group consisting of Titanium Nitride and platinum black.

11. An apparatus according to claim 6 wherein said analysis and display equipment has an input inductance that is sufficiently low enough to prevent distortion of an electrical signal sensed by said electrode.

12. A method of electrophysiological mapping comprising:
   a. Preparing a catheter having a distal portion;
   b. Affixing an electrode substrate to said distal portion;
   c. Coating said electrode substrate with a material providing a micro textured surface which increases the effective surface area while reducing the amount of capacitive coupling;

d. Coupling said catheter to analysis and display equipment;

e. Inserting said catheter into a patient such that said electrode contacts myocardial tissue of said patient;

f. Generating an electrophysiologic map using said analysis and display equipment based on electrical signals produced by said catheter; and g. Removing said catheter.

13. A method according to claim 12 wherein said coating step further comprises sintering said material to said substrate.

14. A method according to claim 13 wherein said inserting step further comprises repeatedly repositioning said catheter such that said electrode contacts myocardial tissue at multiple locations.

15. An apparatus comprising:

a. Means for analysis and display;

b. Means responsively coupled to said analysis and display means for coupling a sensed signal from a distal portion thereof to said analysis and display means, said distal portion being adapted for insertion into the myocardium; and c. Means responsively coupled to said distal portion for presenting a micro textured surface which increases the effective surface area while reducing the amount of capacitive coupling.

16. An apparatus according to claim 15 wherein said presenting means further comprises:

a. Means for providing a substrate; and b. Means for coating said providing means with said micro textured surface.

17. An apparatus according to claim 16 wherein said substrate providing means further comprises a surface selected from the group consisting of smooth surface, porous surface, and textured surface.

18. An apparatus according to claim 17 wherein said substrate providing means further comprises a shape selected from the group consisting of a spherical shape, a semi-spherical shape, a ring shape, and a partial ring shape.

19. An apparatus according to claim 18 wherein said coating means further comprises a coating selected from the group consisting of Titanium Nitride and platinum black.

* * * * *